United States Patent [19]

Noveroske

[11] Patent Number: 5,262,380
[45] Date of Patent: Nov. 16, 1993

[54] HERBICIDAL COMPOSITIONS WITH INCREASED CROP SAFETY

[75] Inventor: Robert L. Noveroske, Midland, Mich.

[73] Assignee: DowElanco, Indianapolis, Ind.

[21] Appl. No.: 857,030

[22] Filed: Mar. 24, 1992

Related U.S. Application Data

[63] Continuation-in-part of Ser. No. 695,193, May 3, 1991, abandoned.

[51] Int. Cl.$^5$ ........................ A01N 25/32; A01N 43/54
[52] U.S. Cl. ...................................... 504/110; 504/136; 504/146; 504/215; 504/323
[58] Field of Search ................ 71/92, 117; 504/110, 504/136, 146, 215, 323

[56] References Cited

U.S. PATENT DOCUMENTS

| | | | |
|---|---|---|---|
| Re. 23,115 | 5/1949 | Lontz | 71/117 |
| 2,390,941 | 12/1945 | Jones | 71/117 |
| 3,131,509 | 5/1964 | Hoffmann | 47/1 |
| 3,929,452 | 12/1975 | Kimura et al. | 71/100 |
| 4,127,405 | 11/1978 | Levitt | 71/93 |
| 4,170,464 | 10/1979 | Feeney | 71/92 |
| 4,547,215 | 10/1985 | Wolf | 71/92 |
| 4,734,123 | 3/1988 | Monte | 71/92 |
| 4,818,273 | 4/1989 | Kleschick et al. | 71/90 |
| 4,840,663 | 6/1989 | Quadranti et al. | 71/93 |
| 4,936,900 | 6/1990 | Hyson | 71/90 |

OTHER PUBLICATIONS

The Agrochemicals Handbook, 2nd edition–"2,4,-D" (Aug. 87).

*Primary Examiner*—Glennon H. Hollrah
*Assistant Examiner*—B. Bembenick
*Attorney, Agent, or Firm*—S. Preston Jones

[57] ABSTRACT

Disclosed are herbicidal concentrate formulation compositions having reduced crop plant phytotoxicity comprising N-(2,6-difluorophenyl)-5-methyl-1,2,4-triazolo(1,5-a) pyrimidine-2-sulfonamide or an amine salt thereof in admixture with one or more amine salts of 2,4-D; also disclosed is the preparation of said compositions and the pre- and post-emergent agricultural uses thereof in water diluted form.

33 Claims, No Drawings

HERBICIDAL COMPOSITIONS WITH INCREASED CROP SAFETY

This application is a continuation-in-part of Ser. No. 07/695,193, filed May 3, 1991, now abandoned.

FIELD OF THE INVENTION

The present invention is directed to corn and sorghum selective pre- and post-emergent herbicidal concentrate formulation compositions comprising N-(2,6-difluorophenyl)-5-methyl-1,2,4-triazolo-1,5-a)-pyrimidine-2-sulfonamide or an amine salt thereof in admixture with one or more amine salts of 2,4-D; the preparation of said concentrates and the pre- and post-emergent agricultural uses of said concentrates in water diluted form.

BACKGROUND OF THE INVENTION

Various herbicides, such as, for example, those of the sulfonamide classes are known to be active as selective pre- and post-emergent weed control agents. Many times when certain of these compounds are employed at the dosage rates usually necessary for the control of many of the broadleaf and/or grassy weeds, serious loss of some sensitive broadleaf and/or grassy crop plants occur.

One procedure to overcome the above indicated sensitivity responses of plants to the various herbicidal compounds involves varying the dosage rate. When a reduction in the dosage rate is used to avoid phytotoxicity to the crop plants, reduced weed control is often the result.

Another procedure involves changing the time of application or modifying the ingredients used in the formulations containing the active compound. Other known procedures include treatment of the seeds of the crop plants with an agent antagonistic to the herbicide prior to planting as described in U.S. Pat. No. 3,131,509.

It has now been found that the post-emergent phytotoxicity of the herbicide N-(2,6-difluorophenyl)-5-methyl-1,2,4-triazolo(1,5-a)pyrimidine-2-sulfonamide toward grass crop plants is reduced by admixing said herbicide with one or more amine salts of 2,4-D in an amount sufficient to maintain the pH of the mixture above 6 and up to about 12. It has further been discovered that esters of 2,4-D do not offer the same protection to the crop plants as afforded by the amine salts.

DESCRIPTION OF KNOWN PRIOR ART

U.S. Pat. No. 4,127,405 is directed to certain sulfonamides/sulfonylureas and their use as selective herbicides. It is further indicated that the claimed compounds can be used in combination with other herbicides and 2,4-D and closely related compounds being listed.

U.S. Pat. No. 4,547,215 is directed to certain sulfonamides/sulfonylureas and their use as selective pre- or post-emergent herbicides. It is further indicated that the claimed compounds can be used in combination with other herbicides and 2,4-D is listed.

U.S. Pat. No. 4,840,663 teaches the control of weeds in rice by the use of a synergistic mixture of N-(2-(2-methoxyethoxy)phenylsulfonyl)-N'-(4,6-dimethoxy-1,3,5-triazin-2-yl)urea and a herbicidal compound selected from a large grouping of different types of herbicides. One of the grouping includes 2,4-D.

U.S. Pat. No. 4,936,900 is directed to stabilized compositions having a pH of 6–10 and containing a mixture of a sulfonylurea or one of its agriculturally suitable salts with a salt or mixture of salts of a carboxylic or inorganic acid. It is further indicated that other herbicides may be added to the mixture and a very large list of other herbicides which may be added is set forth which includes, for example, 2,4-D and its agriculturally suitable salts and esters. It is noted that in this patent the pH is maintained by a material other than the agriculturally suitable salts and esters of 2,4-D.

SUMMARY OF THE INVENTION

The present invention is directed to herbicidal concentrate compositions containing N-(2,6-difluorophenyl)-5-methyl-1,2,4-triazolo-(1,5-a)-pyrimidine-2-sulfonamide in admixture with one or more amine salts of 2,4-D in an amount sufficient to maintain the pH of the mixture above 6 and up to about 12 and wherein the pH is controlled solely by the amine salt of 2,4-D. The invention is also directed to the preparation of said concentrates, aqueous formulations prepared from said concentrates and the agricultural uses of the thus prepared formulations by applying herbicidally effective amounts of said formulations to plants or their habitat in the pre- and post-emergent kill and control of the weeds present in barley, corn, sorghum and wheat crops.

DESCRIPTION OF SOME PREFERRED EMBODIMENTS

The compositions of the present invention have been found to possess desirable herbicidal activity for use in the post-emergent control of many broadleaf weeds such as velvetleaf, lambsquarter, cocklebur, and buckwheat while showing high selectivity towards barley, corn, sorghum and wheat crop plants.

The amine salts of 2,4-D and the active material found usable in the practice of the present invention are from the group consisting of mono-, di- and tri-$C_1$–$C_4$ alkylamine salts of 2,4-D; and mono-, di- and tri-$C_1$–$C_4$ alkanolamine salts of 2,4-D. Both of the above groups of amine salts, are well known herbicides, many of which can be found in general commerce. Representatives of said salts include the methylamine, dimethylamine, trimethylamine, ethylamine, diethylamine, triethylamine, n-propylamine, di-n-propylamine, tri-n-propylamine, tri-i-propylamine, n-butylamine, di-n-butylamine, tri-n-butylamine, ethanolamine, diethanolamine, triethanolamine and tri-i-propanolamine.

The herbicidally effective amount of N-(2,6-difluorophenyl)-5-methyl-1,2,4-triazolo-1,5-a)-pyrimidine-2-sulfonamide or amine salt thereof in the concentrate composition generally is from about 0.05 to about 90 percent by weight or more. Concentrations from about 2 to about 50 percent by weight are often preferred. The amount of said herbicide present in the final treating composition (mixture) is usually sufficient to provide during post-emergent control of broadleafed weeds from about 1.0 to about 70.0 grams of the said active material per hectare, preferably from about 2.0 to about 35 grams of the said active material per hectare; for pre-emergent control of broadleafed weeds, the active herbicide is provided in an amount of about 10 to about 200 g ai/hectare.

The amount of the amine salt of 2,4-D present in the concentrate composition generally is from about 0.5 to about 80 percent by weight or more. The amount of the amine salt present in the final treating composition (mixture) is sufficient to maintain the pH of the mixture above 6.0 and usually from about pH 6.0 to about 10 and is usually present in an amount sufficient to provide during application, from about 20 to about 2000 grams per hectare.

It is frequently desirable to incorporate a surface active agent in the composition of the present invention. Such surface active or wetting agents can be anionic, cationic or nonionic in character. A suitable list for reference may be found in "McCutcheon's Emulsifiers and Detergents" (1981 Edition).

Examples of anionic surfactants are the calcium and amine salts of dodecylbenzene sulfonic acid and sodium diisooetylsulfosuccinate.

Examples of nonionic surfactants are the condensation products of fatty acid esters, fatty alcohols, fatty acid amides or fatty amines with ethylene and/or propylene oxide, alkyl, alkenyl, or polyaryl-substituted phenols with ethylene and/or propylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, ethoxylated lanolin alcohols or ethoxylated lanolin acids.

Representative of the above surface active or wetting agents useful in the practice of the present invention include products such as, for example:

PG 26-2: a secondary butyl(((phenoxy(polypropylene)oxy)polyethylene)oxy) ethanol (5 moles EO,4 moles PO) a product of The Dow Chemical Co.

TRITON (Ortho) X-77: alkylarylpolyoxyethylene glycol, a product of Chevron Chemical Co.

SILWET L-77: nonionic silicone glycol copolymer; a product of Union Carbide Corp.

Examples of a cationic agent include, for instance, an aliphatic mono-, di- or polyamine as an acetate or oleate.

Anionic/nonionic blends are preferred and are often advantageously chosen as pre-blended systems for ease of handling, reproducibility and cost effectiveness.

The choice of suitable surfactants to achieve this is well within the capabilities of one skilled in the art.

The amount of surfactant present in the concentrate composition will generally be in the range of from about 0.0 percent to about 10 percent, preferably from 1.0 percent to 7.0 percent by weight. The amount of surfactant present in the final treating composition (mixture) is usually from about 0.0 to about 5.0 percent by weight, preferably from 0.0 percent to 0.5 percent by weight.

In the agricultural uses set forth hereinabove, the present invention also embraces the employment of the present herbicides in combination with one or more additional pesticidal compounds. Such additional pesticidal compounds may be other types of herbicides, insecticides, nematocides, miticides, arthropodicides, fungicides or bactericides that are compatible with the compounds of the present invention in the aqueous medium used for application and which are not antagonistic to the activity of the compounds employed in the present concentrate. Accordingly, in such embodiments, the additional pesticidal compound(s) is employed as a supplemental toxicant or as an additament. The added compounds in combination with the compounds of the concentrate can generally be present in a ratio of from 1 to 100 parts of the compounds of concentrate of the present invention with from 100 to 1 part of the additional compound.

The exact herbicidally effective amount of the composition to be applied is dependent not only on the specific active ingredient contained therein, but also on the particular action desired, the plant species to be controlled, the stage of growth thereof as well as the specific part of the plant to be contacted.

The following examples illustrate the present invention and the manner by which it can be practiced but, as such, should not be construed as limitations upon the overall scope of the same. In addition, the pH value given is taken from the run with the highest 2,4-D amine concentration and the pH of all runs is greater than 6.0.

EXAMPLE I

Representative compositions of the present invention were evaluated to determine their phytotoxicity effect in post-emergent operations on corn plants.

Aqueous dispersions containing N-(2,6-difluorophenyl)-5-methyl-1,2,4-triazolo-(1,5-a)pyrimidine-2-sulfonamide, as the active ingredient, were prepared by admixing a predetermined amount of the compound with a predetermined quantity of water, a predetermined amount of a 50:50 mixture of the dimethylamine salt of 2,4-D and tri-i-propanolamine salt of 2,4-D and a predetermined amount of the surfactant X-77 to give aqueous dispersions containing varying amounts of the compound, as the sole toxicant.

Corn seeds were planted in beds of good agricultural peat based soil and grown in a greenhouse. After the plants had emerged and had grown to a height of about 4 inches, separate beds of the plants were sprayed with one of the above-prepared compositions at a predetermined treating rate in grams of the active ingredient per hectare (g ai/ha). Other beds were treated only with a water-surfactant mixture, containing no active compound, and others containing the active compound and surfactant, but no amine salt, to serve as controls. After treatment, the beds were maintained for seven days under greenhouse conditions conducive for good plant growth. At the end of this period, the beds were examined to determine the percentage of phytotoxicity to the corn plants. The results of these examinations are set forth below in Table I.

TABLE I

| Test mixture | treating rate in g amine salt/ha | pH | % growth reduction as a % of control at indicated g ai/ha* | | |
|---|---|---|---|---|---|
| | | | 35.0 | 17.5 | 8.8 |
| N-(2,6-difluorophenyl)-5-methyl-1,2,4-triazolo-(1,5-a)-pyrimidine-2-sulfonamide/NA | — | 7.48 | 10.0 | 10.0 | 10.0 |
| N-(2,6-difluorophenyl)-5-methyl-1,2,4-triazolo-1,5-a)-pyrimidine-2-sulfonamide + 2,4-D: dimethylamine salt/tri-i propanolamine salt | 430.0 | 7.62 | 0.0 | 0.0 | 0.0 |
| N-(2,6-difluorophenyl)-5-methyl-1,2,4-triazolo-1,5-a)-pyrimidine-2-sulfonamide + 2,4-D: dimethylamine salt/tri-i propanolamine salt | 215.0 | 7.43 | 0.0 | 0.0 | 0.0 |
| N-(2,6-difluorophenyl)-5-methyl-1,2,4-triazolo-1,5-a)-pyrimidine-2-sulfonamide + 2,4-D: dimethylamine salt/tri-i | 107.5 | 7.25 | 5.0 | 5.0 | 5.0 |

TABLE I-continued

| Test mixture | treating rate in g amine salt/ha | pH | % growth reduction as a % of control at indicated g ai/ha* | | |
|---|---|---|---|---|---|
| | | | 35.0 | 17.5 | 8.8 |
| propanolamine salt control | — | 7.83 | 0.0 | 0.0 | 0.0 |

NA = no amine control
*= grams of active ingredient per hectare.

EXAMPLE II

Representative compositions of the present invention were evaluated to determine their phytotoxicity effect in post-emergent operations on sorghum plants.

Aqueous dispersions containing N-(2,6-difluorophenyl)-5-methyl-1,2,4-triazolo-(1,5-a)-pyrimidine-2-sulfonamide, as the active ingredient, were prepared by admixing a predetermined amount of the compound with a predetermined quantity of water, a predetermined amount of a 50:50 mixture of the dimethylamine salt of 2,4-D and tri-i-propanolamine salt of 2,4-D and a predetermined amount of the surfactant X-77 to give aqueous dispersions containing varying amounts of the compound, as the sole toxicant.

Sorghum was planted in beds of good agricultural peat based soil and grown in a greenhouse. After the plants had grown to a height of about 3–4 inches, separate beds of the plants were sprayed with one of the above-prepared compositions at a predetermined treating rate in grams of the active ingredient per hectare (g ai/ha). Other beds were treated only with a water-surfactant mixture, containing no active compound, and others containing the active compound and surfactant, but no amine, to serve as controls. After treatment, the beds were maintained for 13 days under greenhouse conditions conducive for good plant growth. At the end of this period, the beds were examined to determine the percentage of phytotoxicity to the sorghum plants. The results of these examinations are set forth below in Table II.

TABLE II

| Test mixture | treating rate in g amine salt/ha | pH | % Growth reduction as a % of control at indicated g ai/ha* | | |
|---|---|---|---|---|---|
| | | | 35.0 | 11.7 | 3.5 |
| N-(2,6-difluorophenyl)-5-methyl-1,2,4-triazolo-(1,5-a)pyrimidine-2-sulfonamide/NA | — | 7.42 | 90.0 | 85.0 | 65.0 |
| N-(2,6-difluorophenyl)-5-methyl-1,2,4-triazolo-(1,5-a)pyrimidine-2-sulfonamide + 2,4-D | 430.0 | 7.45 | 35.0 | 25.0 | 15.0 |
| N-(2,6-difluorophenyl)-5-methyl-1,2,4-triazolo-(1,5-a)pyrimidine-2-sulfonamide + 2,4-D | 215.0 | 7.43 | 40.0 | 30 | 17.5 |
| control | — | 7.62 | 0.0 | 0.0 | 0.0 |

NA = no acid control
*= grams of active ingredient per hectare.

EXAMPLE III

Representative compositions of the present invention were evaluated to determine their phytotoxicity effect in post-emergent operations on sorghum plants.

Aqueous dispersions containing N-(2,6-difluorophenyl)-5-methyl-1,2,4-triazolo-(1,5-a)-pyrimidine-2-sulfonamide, as the active ingredient, were prepared by admixing a predetermined amount of the compound with a predetermined quantity of water, a predetermined amount of a 50:50 mixture of the dimethylamine salt of 2,4-D and tri-i-propanolamine salt of 2,4-D and a predetermined amount of the surfactant X-77 to give aqueous dispersions containing varying amounts of the compound, as the sole toxicant.

Sorghum was planted in beds of good agricultural peat based soil and grown in a greenhouse. After the plants had grown to a height of about 3–4 inches, separate beds of the plants were sprayed with one of the above-prepared compositions at a predetermined treating rate in grams of the active ingredient per hectare (g ai/ha). Other beds were treated only with a water-surfactant mixture, containing no active compound, and others containing the active compound and surfactant, but no amine, to serve as controls. After treatment, the beds were maintained for five days under greenhouse conditions conducive for good plant growth. At the end of this period, the beds were examined to determine the percentage of phytotoxicity to the sorghum plants. The results of these examinations are set forth below in Table III.

TABLE III

| Test mixture | treating rate in g amine salt/ha | pH | % Growth reduction as a % of control at indicated g ai/ha* | | |
|---|---|---|---|---|---|
| | | | 8.8 | 4.4 | 2.2 |
| N-(2,6-difluorophenyl)-5-methyl-1,2,4-triazolo-(1,5-a)pyrimidine-2-sulfonamide/NA | — | 7.83 | 50.0 | 50.0 | 42.5 |
| N-(2,6-difluorophenyl)-5-methyl-1,2,4-triazolo-(1,5-a)pyrimidine-2-sulfonamide + 2,4-D | 430.0 | 7.75 | 15.0 | 10.0 | 0.0 |
| N-(2,6-difluorophenyl)-5-methyl-1,2,4-triazolo-(1,5-a)pyrimidine-2-sulfonamide + 2,4-D | 215.0 | 7.72 | 15.0 | 10.0 | 0.0 |
| N-(2,6-difluorophenyl)-5-methyl-1,2,4-triazolo-(1,5-a)pyrimidine-2-sulfonamide + 2,4-D | 107.5 | 7.71 | 20.0 | 15.0 | 10.0 |
| control | — | 7.88 | 0.0 | 0.0 | 0.0 |

NA = no acid control
*= grams of active ingredient per hectare.

What is claimed is:

1. A formulation concentrate herbicidal composition comprising, as the active material, a herbicidally effective amount of N-(2,6-difluorophenyl)-5-methyl-1,2,4-triazolo-1,5-a)-pyrimidine-2-sulfonamide or an amine salt thereof in admixture with an amount of an amine salt of 2,4-D acid sufficient to maintain the pH of the composition above 6.0 and up to about 12.

2. A composition as defined in claim 1 wherein the amine salt is a mono-, di- or tri-$C_1$-$C_4$ alkylamine salts of 2,4-D.

3. A composition as defined in claim 1 wherein the amine salt is the dimethylamine salt of 2,4-D.

4. A composition as defined in claim 1 wherein the amine salt is the trimethylamine salt of 2,4-D.

5. A composition as defined in claim 1 wherein the amine salt is the tri-i-propylamine salt of 2,4-D.

6. A composition as defined in claim 1 wherein the amine salt is a mixture of at least one mono-, di- or tri-$C_1$-$C_4$ alkylamine salt of 2,4-D.

7. A composition as defined in claim 1 wherein the amine salt is a mono-, di- or tri-$C_1$-$C_4$ alkanolamine salts of 2,4-D.

8. A composition as defined in claim 1 wherein the amine salt is the diethanolamine salt of 2,4-D.

9. A composition as defined in claim 1 wherein the amine salt is the triethanolamine salt of 2,4-D.

10. A composition as defined in claim 1 wherein the amine salt is the tri-i-propanolamine salt of 2,4-D.

11. A composition as defined in claim 1 wherein the amine salt is a mixture of amine salts of which at least one is a mono-, di- or tri-$C_1$–$C_4$ alkanolamine salt of 2,4-D.

12. An aqueous herbicide formulation composition comprising, as the active material, a herbicidally effective amount of N-(2,6-difluorophenyl)-5-methyl-1,2,4-triazolo-(1,5-a)-pyrimidine-2-sulfonamide or an amine salt thereof in admixture with an amount of an amine salt of 2,4-D acid sufficient to maintain the pH of the composition above 6.0 and up to about 12 and water.

13. A composition as defined in claim 7 wherein the amine salt is a mono-, di- or tri-$C_1$–$C_4$ alkylamine salts of 2,4-D.

14. A composition as defined in claim 8 wherein the amine salt is the dimethylamine salt of 2,4-D.

15. A composition as defined in claim 8 wherein the amine salt is the trimethylamine salt of 2,4-D.

16. A composition as defined in claim 8 wherein the amine salt is the tri-i-propylamine salt of 2,4-D.

17. A composition as defined in claim 8 wherein the amine salt is a mixture of at least one mono-, di- or tri-$C_1$–$C_4$ alkylamine salt of 2,4-D.

18. A composition as defined in claim 7 wherein the amine salt is a mono-, di- or tri-$C_1$–$C_4$ alkanolamine salts of 2,4-D.

19. A composition as defined in claim 13 wherein the amine salt is the diethanolamine salt of 2,4-D.

20. A composition as defined in claim 13 wherein the amine salt is the triethanolamine salt of 2,4-D.

21. A composition as defined in claim 13 wherein the amine salt is the tri-i-propanolamine salt of 2,4-D.

22. A composition as defined in claim 13 wherein the amine salt is a mixture of amine salts of which at least one is a mono-, di- or tri-$C_1$–$C_4$ alkanolamine salt of 2,4-D.

23. A method for reducing the phytotoxicity toward grassy crop plants of N-(2,6-difluorophenyl)-5-methyl-1,2,4-triazolo(1,5-a)pyrimidine-2-sulfonamide or an amine salt thereof employed in the selective kill and control of broadleaf weeds growing in the presence of said grassy crop plants which comprises contacting said plants or their habitat with a herbicidally effective amount of a formulation containing, as the active material, said compound in admixture with an amount of an amine salt of 2,4-D sufficient to maintain the pH of the composition above 6.0 and up to about 12 and water.

24. A method as defined in claim 18 wherein the amine salt is a mono-, di- or tri-$C_1$–$C_4$ alkylamine salts of 2,4-D.

25. A method as defined in claim 19 wherein the amine salt is the dimethylamine salt of 2,4-D.

26. A method as defined in claim 19 wherein the amine salt is the trimethylamine salt of 2,4-D.

27. A method as defined in claim 19 wherein the amine salt is the tri-i-propylamine salt of 2,4-D.

28. A method as defined in claim 19 wherein the amine salt is a mixture of at least one mono-, di- or tri-$C_1$–$C_4$ alkylamine salt of 2,4-D.

29. A method as defined in claim 18 wherein the amine salt is a mono-, di- or tri-$C_1$–$C_4$ alkanolamine salts of 2,4-D.

30. A method as defined in claim 24 wherein the amine salt is the diethanolamine salt of 2,4-D.

31. A method as defined in claim 24 wherein the amine salt is the triethanolamine salt of 2,4-D.

32. A method as defined in claim 24 wherein the amine salt is the tri-i-propanolamine salt of 2,4-D.

33. A method as defined in claim 24 wherein the amine salt is a mixture of amine salts of which at least one is a mono-, di- or tri-$C_1$–$C_4$ alkanolamine salt of 2,4-D.

* * * * *